United States Patent [19]

Sandmeier et al.

[11] Patent Number: 4,472,425
[45] Date of Patent: Sep. 18, 1984

[54] THIOPHENE DERIVATIVES

[75] Inventors: Rudolf Sandmeier, Binningen, Switzerland; Karl Seckinger, Riegel, Fed. Rep. of Germany

[73] Assignee: Sandoz Ltd., Basel, Switzerland

[21] Appl. No.: 529,398

[22] Filed: Sep. 6, 1983

[30] Foreign Application Priority Data

Sep. 13, 1982 [GB] United Kingdom ............... 8226005

[51] Int. Cl.$^3$ .................. A01N 43/02; A01N 43/48; C07D 233/00; C07D 231/00
[52] U.S. Cl. .................... 424/275; 424/269; 424/270; 424/272; 424/273 P; 424/273 R; 548/229; 548/230; 548/240; 548/269; 548/300; 548/356; 548/373; 548/379; 548/527; 549/38; 549/60; 549/63; 549/69
[58] Field of Search ........... 424/269, 270, 272, 273 R, 424/273 P, 275; 548/229, 230, 240, 269, 300, 356, 373, 379, 527; 549/38, 60, 63, 69

[56] References Cited

U.S. PATENT DOCUMENTS

| 3,823,161 | 7/1974 | Lesser | 549/69 |
| 4,240,820 | 12/1980 | Dickore et al. | 549/69 |
| 4,260,410 | 4/1981 | Schinski | 549/69 |

Primary Examiner—Alan Siegel
Attorney, Agent, or Firm—Gerald D. Sharkin; Richard E. Vila

[57] ABSTRACT

The invention provides novel N-acylamino thiophene derivatives, e.g. N-(methoxyacetyl)-N-(5-bromo-4-methyl-2-methylthiothien-3-yl)alanine methyl ester, which are useful as fungicides. Other objects of the invention are fungicidal compositions comprising such novel compounds and methods of combatting phytopathogenic fungi with the acid of said novel compounds.

10 Claims, No Drawings

THIOPHENE DERIVATIVES

The present invention relates to novel thiophene derivatives, their use as fungicides, compositions for facilitating such use and the preparation of these thiophene derivatives and of compositions containing such compounds.

The invention provides compounds of formula I

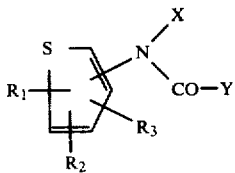

wherein $R_1$, $R_2$ and $R_3$, independently, are H, $C_{1-4}$alkyl, $C_{1-4}$alkoxy, $C_{1-4}$alkylthio or halogen selected from F, Cl and Br, X is selected from a group —CH($R_4$)—$R_5$ or a group —N($R_6$)—COO$R_7$, in which $R_4$ is H or $C_{1-4}$alkyl, $R_5$ is COZ$R_8$, CO—N($R_9$)O$R_{10}$, CN, CHO,

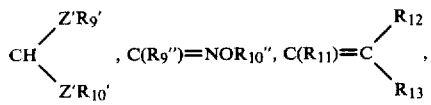

C≡C—$R_{14}$, allenyl; or is 2,2-dihalo-1-cyclopropyl unsubstituted or substituted by $C_{1-4}$alkyl; or is phenyl unsubstituted or substituted, $R_6$ is $C_{1-3}$alkyl, $R_7$ is $C_{1-6}$alkyl, $C_{3-6}$alkenyl or $C_{3-6}$alkinyl, whereby $R_6$ and $R_7$ may be linked together to form $CH_2$—$CH_2$;

and wherein

Z and Z' are O or S $R_8$ is $C_{1-6}$alkyl, $C_{3-6}$alkenyl, or $C_{3-6}$alkinyl, and whereby Z$R_8$ may be linked with $R_4$ to form the bridge ZCH($R_{15}$)—$CH_2$ in which Z is as defined above and $R_{15}$ is H or $CH_3$;

$R_9$, $R'_9$ and $R''_9$ are H or $C_{1-4}$alkyl, $R_{10}$, $R'_{10}$ and $R''_{10}$ are $C_{1-4}$alkyl, whereby $R_9$ may be linked with $R_{10}$, resp. $R'_9$ with $R'_{10}$, resp. $R''_9$ with $R''_{10}$ and signify alkylene, to form a 5- or 6-membered heterocyclic ring, $R_{11}$, $R_{12}$, $R_{13}$, independently, are H, $C_{1-4}$alkyl, or halogen selected from F, Cl or Br, $R_{14}$ is H, $C_{1-4}$alkyl or halogen selected from Cl, Br or I, and Y is H;

a hydrocarbon selected from $C_{1-6}$alkyl, $C_{2-6}$alkenyl and $C_{2-6}$alkinyl unsubstituted or substituted by halogen, selected from F, Cl or Br, or by CN;

$C_{2-6}$epoxyalkylene; $C_{3-6}$cycloalkyl; a 5-membered heterocyclic ring comprising 1 to 3 heteroatoms selected from O, S and N, which in unsubstituted or substituted by $C_{1-4}$alkyl or halogen selected from F, Cl or Br;

$(A)_n$—Az; $(A)_n$—$Y_1$—NR$_{9a}$R$_{10a}$;

$(A)_nZ_1H$ and esters or ethers thereof;

benzyl unsubstituted or substituted, in which

A is $CH_2$ or $CH(CH_3)$ n is 0 or 1,

Az is a 1-azolyl comprising 1 to 3 nitrogen atoms, $Y_1$ is a covalent bond or NH, $R_{9a}$ is H or $C_{1-4}$alkyl, $R_{10a}$ is $C_{1-4}$alkyl, $Z_1$ is O or S.

Where any of $R_1$, $R_2$, $R_3$ and $R_4$ is or comprises $C_{1-4}$alkyl, this is preferably $CH_3$.

Where $R_5$ is 2,2-dihalo-1-cyclopropyl both halogens comprised therein signify F, Cl or Br, particularly Cl or Br, especially Cl; both halogens are preferably identical. Any $C_{1-4}$alkyl substituent of 2,2-dihalo-1-cyclopropyl signifies preferably $CH_3$.

Where $R_5$ is substituted phenyl, it is conveniently mono- or disubstituted. Suitable substituents of phenyl are e.g. $C_{1-4}$alkyl ($CH_3$), $C_{1-4}$alkoxy ($OCH_3$) and halogen (F, Cl, Br).

$R_6$ is preferably $CH_3$.

Where any of $R_7$ and $R_8$ is $C_{1-6}$alkyl, it is conveniently $C_{1-3}$alkyl, preferably $CH_3$.

Where any of $R_9$, $R'_9$, $R''_9$, $R_{10}$, $R'_{10}$ and $R''_{10}$ s $C_{1-4}$alkyl, it is e.g. $CH_3$.

Where $R_9$ and $R_{10}$, resp. $R'_9$ and $R'_{10}$ resp. $R''_9$ and $R''_{10}$ are linked together and represent alkylene, such alkylene is conveniently unbranched.

Where any of $R_{11}$, $R_{12}$ and $R_{13}$ is $C_{1-4}$alkyl, this is preferably $CH_3$.

Where any of $R_{11}$, $R_{12}$ and $R_{13}$ is halogen, this is preferably Cl or Br, particularly Cl.

Where $R_{14}$ is $C_{1-4}$alkyl, this may be straight or branched and signifies for example $CH_3$.

Where Y is hydrocarbon substituted by halogen, such halogen is conveniently Cl or Br.

Where Y is substituted hydrocarbon, the hydrocarbon signifies preferably $C_{1-6}$alkyl, particularly $C_{1-3}$alkyl.

Where Y is $C_{1-6}$alkyl, unsubstituted, it is preferably $C_{3-5}$alkyl, particularly unbranched $C_{3-5}$alkyl or 2-methyl-1-butyl.

Where Y is $C_{3-6}$alkenyl, it is preferably CH=CH—$CH_3$.

Where Y is $C_{3-6}$cycloalkyl, it is preferably cyclopropyl or cyclobutyl.

Where Y is a 5-membered heterocycle, this may be aromatic oder hydrogenated; examples of suitable heterocyclic radicals are furyl (e.g. 2-furyl), tetrahydrofuryl, thienyl, isoxazyl and thiadiazolyl. Suitable substituents of such heterocyclic groups are particularly Cl, Br, $CH_3$. Any substituted heterocycle is particularly monosubstituted.

Suitable significances of Az are e.g. pyrazol-1-yl, imidazol-1-yl and 1H-1,2,4-triazol-1-yl.

Where $R_{9a}$ is $C_{1-4}$alkyl, this is especially $CH_3$ or $C_2H_5$.

$R_{10a}$ signifies preferably $CH_3$.

Suitable examples of compounds of formula I, wherein Y is esterified $(A)_nZ_1H$ are esters with an alkane carboxylic acids (such as $CH_3COOH$), an alkane sulfonic acid (e.g. $CH_3SO_2OH$), a dialkylsulfamic acid (e.g. $(CH_3)_2NSO_2OH$), a functional derivative of a carbonic acid etc.

Suitable examples of compounds of formula I, wherein Y is etherified $(A)_nZ_1H$ are e.g. compounds of formula I, wherein Y is $(A)_nZ_1W$, in which A, n and $Z_1$ are as defined above and W is a group selected from $C_{1-8}$alkyl (particularly $CH_3$, $C_2H_5$), $C_{3-6}$alkenyl (particularly $CH_2$—$CH=CH_2$), $C_{3-6}$alkinyl (particularly $CH_2C\equiv CH$), $C_{1-4}$alkoxy-$C_{1-3}$alkyl, (particularly $CH_2OCH_3$), $C_{1-4}$alkythio-$C_{1-3}$alkyl (particularly $CH_2SCH_3$) unsubstituted or substituted by halogen (F, Cl, Br) or a pyranyl group.

Preferred compounds of formula I have one or more of the following features:
the group N(X)—COY is in the 3-position of the thiophene ring
$R_3$ is hydrogen, Cl or Br,
$R_3$ is Br,
$R_1$ is in o-position of N((X)—COY,
$R_1$ and $R_2$ are in o,o'-position of N(X)COY,
$R_1$ and $R_2$ are selected from $CH_3$, Cl, $OCH_3$ and $SCH_3$,
at least one of $R_1$ and $R_2$ is $OCH_3$ or $SCH_3$
X is $CH(R_4)COZR_8$, $N(CH_3)$—$COOC_{1-6}$alkyl,
$R_4$ is $CH_3$,
Z and Z' are O,
$R_8$ is $C_{1-6}$alkyl,
$R_8$ is linked with $R_4$ to form $CH_2CH_2$,
X is $CH(CH_3)COOCH_3$,
X is tetrahydro-2-furanone-3-yl,
X is 2-oxo-3-oxozolidinyl,
X is $N(CH_3)COOCH_3$,
X is $CH_2OH$, $CH_2OCH_3$, $CH_2OC_2H_5$, $CH_2O$—$CH_2$—$CH=CH_2$, $CH_2O$—$CH_2$—$C\equiv CH$, $CH_2$—$OCH_2OCH_3$, $CH_2OSO_2N(CH_3)_2$, $CH_2Cl$, n—$C_3H_7$, n—$C_4H_9$, cyclopropyl, $CH=CH$—$CH_3$, 2-furyl, benzyl or 2-tetrahydrofuryl.

The invention also provides processes for the production of compounds of formula I, which comprises:
(a) obtaining a compound of formula Ia

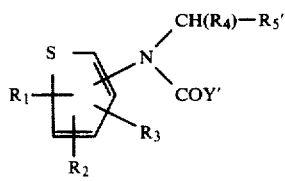

wherein
$R'_5$ has the meaning of $R_5$, defined above, with the exception of allenyl,
Y' has the meaning of Y, defined above, with the exception of $CH_2Z_1H$, $AY_1NR_{9a}R_{10a}$ and $C_{2-6}$epoxyalkylene,
and $R_1$, $R_2$, $R_3$, $R_4$, $Z_1$,A,$Y_1$, $R_{9a}$ and $R_{10a}$ are as defined above by N-acylating a compound of formula II,

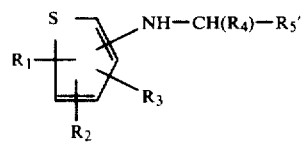

wherein $R_1$, $R_2$, $R_3$, $R_4$ and $R_5$ are as defined above, with a compound of formula III $$Y'—CO—E \qquad III$$

wherein
E is halogen or Y'—COO,
and Y' is as defined above, (b) obtaining a compound of formula Ia, as defined above,
by reacting a compound of formula IV

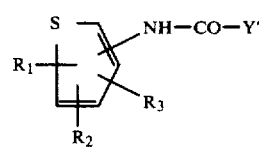

wherein $R_1$, $R_2$, $R_3$ and Y' are as defined above, with a compound of formula V

wherein
$R_4$ and $R'_5$ are as defined above and
L is a leaving group capable of being split off under the reaction conditions, (c) obtaining a compound of formula Ib

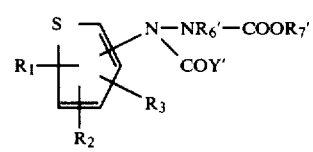

wherein
$R_1$, $R_2$, $R_3$ and Y' are as defined above,
and $R'_6$ and $R'_7$ are as defined above, with the exception that $R'_6$ and $R'_7$ are not $CH_2$—$CH_2$,
by N-alkylating a compound of formula VI

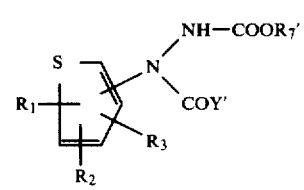

wherein $R_1$, $R_2$, $R_3$, $R'_7$ and Y' are as defined above, in salt form, with a compound of formula VII

wherein $R'_6$ and L are as defined above,
(d) obtaining a compound of formula Ic

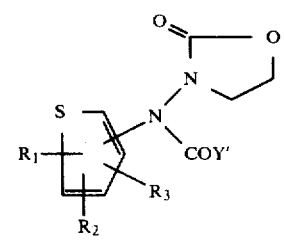

wherein $R_1$, $R_2$, $R_3$ and Y' are as defined above, by subjecting a compound of formula VIII

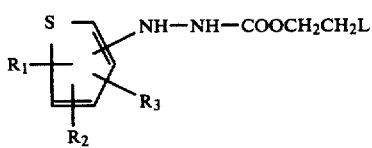

wherein $R_1$, $R_2$, $R_3$ and L are as defined above in any chosen order to
(α) an N-acylation, using the compound of formula III, defined above as acylating agent and to
(β) a base promoted ring closure,
(e) obtaining a compound of formula Id

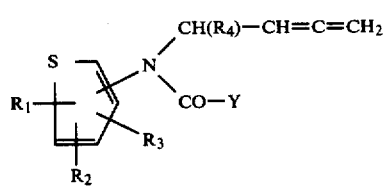

wherein $R_1$, $R_2$, $R_3$, $R_4$ and Y are as defined above, by treating a compound of formula Ie

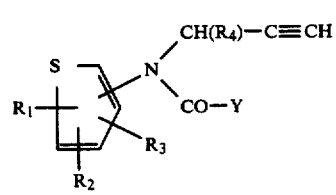

wherein $R_1$, $R_2$, $R_3$, $R_4$ and Y are as defined above with $CH_2O$, under the conditions necessary for the conversion of an acetylene group to an allene group,
(f) obtaining a compound of formula If

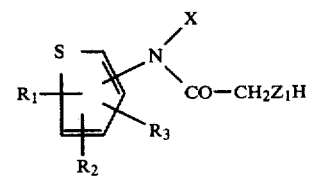

wherein $R_1$, $R_2$, $R_3$, $Z_1$ and X are as defined above, by base catalysed alcoholysis of the corresponding esters (hereinafter compounds of formula Ig),
(g) obtaining a compound of formula Ih

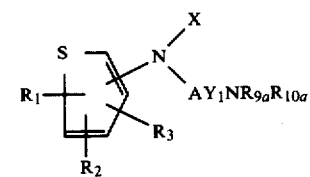

wherein $R_1$, $R_2$, $R_3$, A, $R_{9a}$, $R_{10a}$, $Y_1$ and X are as defined above by nucleophilic substitution of the group L in a compound of formula IX

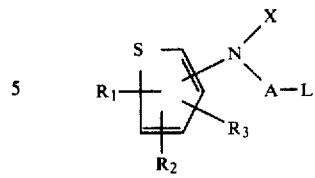

wherein $R_1$, $R_2$, $R_3$, A, X and L are as defined above by reaction with the nucleophile of formula X

wherein
$R_{9a}$ and $R_{10a}$ are as defined above,
$Y'_1$ is H or $NH_2$,
(h) obtaining a compound of formula Ii

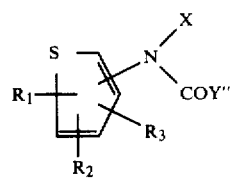

wherein
Y″ is $C_{2-6}$epoxyalkylene
and X, $R_1$, $R_2$ and $R_3$ are as defined above, by epoxydation of the corresponding alkenyl compounds of formula Ij

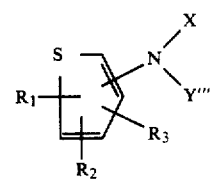

wherein
$R_1$, $R_2$, $R_3$ and X are as defined above
and Y‴ is $C_{2-6}$alkenyl,
(i) obtaining a compound of formula Ik

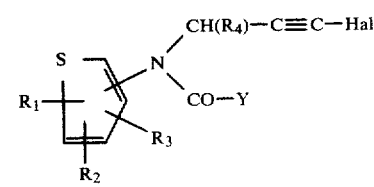

wherein
$R_1$, $R_2$, $R_3$, $R_4$ and Y are as defined above and
Hal is halogen selected from Cl, Br and I,
by substituting in a compound of formula Ie, as defined above, the acetylenic hydrogen by Hal.

The processes of the invention may be carried out in conventional manner.

The N-acylation according to process (a) is conveniently effected in a solvent which is inert under the reaction conditions. Suitable solvents are e.g. aromatic or halogenated hydrocarbons such as toluene and chlorobenzene or dichloromethane. Where E is halogen, this signifies preferably chlorine. The presence of a base such as NaHCO₃, triethylamine is advantageous, particularly where E is halogen. A suitable reaction temperature is from 0° to 110° C., e.g. 20° to 30° C.

The compounds of formula IV, when reacted according to process (b) may be used in free (acid) form or salt form, e.g. the alkali-metal salt form (such as the Na salt). Such salt forms are obtained from the corresponding amides of formula IV in acid form by reaction with an appropriate base, e.g. sodium hydride, in a solvent which is inert under the reaction conditions, such as a dialkylamide of a carboxylic acid or an aromatic hydrocarbon, e.g. dimethylformamide or toluene. The reaction of the compound of formula IV in salt form with a compound of formula V proceeds smoothly, in general even at room temperature; it is suitably effected by adding a compound of formula V to the above described solution of the compound of formula IV in salt form.

Examples of appropriate meanings of L (compounds of formula V) are halogen, particularly Cl or Br, or alkyl—SO₂O (e.g. mesyloxy) resp. aryl—SO₂O (e.g. tosyloxy).

Process (c) can be effected under similar conditions as indicated for process (b), using the compounds of formula VI in salt form (e.g. Na salt form).

The N-acylation of compounds of formula VIII is also suitably effected in a solvent which is inert under the reaction conditions e.g. toluene, chlorobenzene at a temperature of from about 50° to 120°, e.g. 80° C.

The ring closure of process (d) (step ii)) may be carried out in a water free medium which is inert under the reaction conditions (e.g. dimethoxyethane, toluene) in the presence of an acid binding agent (e.g. sodium hydride, sodium amide, sodium ethylate). The ring closure may, alternatively, also be carried out in an aqueous/organic two-phase system in the presence of an anorganic base (e.g. sodium hydroxide) and, optionally, of a catalytic amount of a phase transfer catalyst.

The conversion of an acetylene compound to an allene compound by reaction with formaldehyde indicated in process (e), is a reaction type known per se (see e.g. EPA 44482). It is conveniently effected in the presence of an amine, e.g. diisopropylamine, and of a suitable catalyst, for example a copper compound such as copper (I) bromide.

The base catalysed alcoholysis according to process (f) is conveniently carried out under mild conditions, e.g. at ambient temperature, preferably in a large excess of an alcohol e.g. methanol and in the presence of a catalytic amount of a sodium alcoholate, e.g. sodium methanolate.

The nucleophilic substitution according to process (g) is conveniently carried out in a solvent which is inert under the reaction conditions, (e.g. in alcohol, hydrocarbon, nitrile or amide such as ethanol, toluene, acetonitril, dimethylformamide) at a temperature between 20° and 110°, e.g. 80° C. The reaction is suitably carried out in the presence of an acid binding agent, such as an organic tert. base. or an inorganic base, e.g. K₂CO₃, or an excess of the compound of formula X.

The epoxydation of compounds of formula Ij according to process (h) is suitably carried out with an organic peroxiacid such as m-chloroperbenzoic acid or with a mixture of hydrogen peroxide and an inorganic base, as e.g. sodium hydroxide.

The substitution of the acetylenic hydrogen in a compound of formula Ie according to process (i) is conveniently effected with the aid of the corresponding hypohalogenic acid which is conveniently prepared in situ, in a manner known per se by reaction of the halogen with an alkali metal hydroxide, such as NaOH.

The componds of formula may be recovered from the reaction mixture in which they are formed by working up by established procedures.

As will be appreciated, interconversion of one compound of formula I to another compound of formula I may be carried out in conventional manner.

Compounds of formula I having an aldehyde function may, for example be obtained by conventional manner from the corresponding acetal, such as its ethylenglycol acetal, by acid catalysed hydrolysis (e.g. with p-toluenesulphonic acid in acetone/water). Compounds of formula I having an oxime function may be obtained by reacting the corresponding aldehyde with the appropriate hydroxylamine. Compounds of formula I having a 2,2-dihalocyclopropyl group may be obtained from the corresponding unsaturated compounds of formula I by reacting with CHCl₃ in the presence of sodiumhydroxide. Where appropriate, compounds of formula If may also be esterified to give the corresponding esters.

The compounds of formula II and IV, which are new, may be obtained from the appropriate amine of formula XI

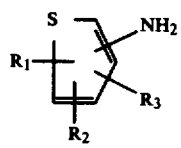

wherein R₁, R₂ and R₃ are as defined above, in conventional manner.

The compounds of formula VI and VIII are obtained in conventional manner from compounds of formula XII

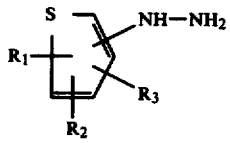

wherein R₁, R₂ and R₃ are as defined above.

The compounds of formula XII are also new. They may be obtained in conventional manner from the corresponding amines of formula XI, e.g. by conversion of formula XI to its diazonium salt by the reaction with sodium nitrite in a hydrochloric acid/water mixture, and reducing the formed diazonium salt in situ with suitable reducing agents, such as SnCl₂, or preferably Na₂SO₃.

The starting materials and reagents employed in the processes described above are either known or, insofar as they are not known, they may be produced in analogous manner to the processes described herein or to known processes.

The compounds of formula I have useful fungicidal activity, particularly against phytopathogenic fungi, especially against fungi of the class Oomycetes as indicated by a significant fungicidal effect in tests against Phytophthora infestans in potatoes (test description, see Test A hereinafter) and against Plasmopara viticola in grape vine (test description, see Test B hereinafter) with concentrations of 8 ppm to 125 ppm, e.g. 8 ppm, 32 ppm and 125 ppm. In view of the test results they are in particular indicated to be useful against resistant Phytophthora and/or Plasmorpara systems. Representative compounds show also interesting activity against Pythium aphanidermatum after soil treatment with concentrations of 10 to 160 ppm, e.g. 32 and 125 ppm (see Test C hereinafter). The compounds of formula I are essentially non-phytotoxic at fungicidally effective doses in plants subject to such fungi and are further indicated to be of particular interest for combatting fungi by systemic, curative and eradicative action. They are also indicated to be useful against particularly resistant Phytophthora and Plasmopara systems.

Test A: Fungicidal effect against *Phytophthora infestans*

Young potted potato plants (3–5 leaf stage) are sprayed until the run off with an aqueous spray suspension containing 0.01% to 0.0008% (weight/volume) of the compound of formula I, formulated for example in accordance with Formulation Example I hereinafter. Two hours later, the treated plants are inoculated with a spore suspension of Phytophthora infestans (approx. $10^5$ sporangia/ml) and the plants are then transferred to a tent providing 100% relative atmospheric humidity at an ambient temperature of 16° C. and 16 hours daylight/day. Disease control is evaluated 4–5 days later by comparing the treated plants with untreated, similarly inoculated plants.

Test B: Fungicidal effect against *Plasmopara viticola*

Young potted plants of grape vine (3–6 leaf stage) are sprayed until the run off with an aqueous spray suspension containing 0.01% to 0.0008% (weight/volume) of a compound of formula I formulated for example in accordance with Formulation Example I hereinafter. Two hours later, the treated plants are inoculated by spray application to the plant of a spore suspension of about $10^5$ sporangia/ml of Plasmopara viticola and the plants are then transferred to a tent providing 100% relative atmospheric humidity at an ambient temperature of 15°–22° C. (fluctuating over a 24 hr-period) and 16 hours daylight/day. Disease control is evaluated 6 days after inoculation by comparing the treated plants with untreated, similarly inoculated plants.

Test C: Soil Treatment

In vivo, employing *Pythium aphanidermatum*. The fungus is cultivated in a sterile mixture of sand and corn meal (97:3 v/v), to which water is added in a ratio of about 1:4(v/v); cultivation lasts for 4 days at 25° C. The fungus is then mixed into a semisterile mixture of peat and sand which then is treated with a suspension containing the formulated active ingredient to give concentration of 10 to 160 ppm (e.g. 10, 40 and 160 ppm) pots of 5 cm diameter which are seeded with cucumber seeds. The planted pots are incubated at 24° C. and 60–70% relative humidity in an incubation chamber for 7 days, after which disease attack is evaluated by a visual determination of the number of healthy emerged plants compared with that in untreated, similarly inoculated check pots.

The compounds of the invention of formula I are therefore indicated for use as fungicide.

The invention therefore also provides a method of combatting phytopathogenic fungi, especially of the class Oomycetes, in a locus (plants, seeds or soil) with a fungicidally effective amount of a compound of formula I.

Fungi of the class Oomycetes, against which the method of the invention is indicated to be particularly effective, are those of the genus Phytophthora in plants such as potatoes, tomatoes, tobacco, citrus, cacao, rubber, applie, strawberries, vegetables and ornamentals, e.g. *Phytophthora infestans* in potatoes and tomatoes; of the genus Plasmopora in plants such as grape vines and sunflower e.g. Plasmopara viticola in grape vines; of the genus Peronospora in plants such as tobacco, e.g. *Peronospora tabacina* in tobacco; of the genus Pseudoperonospora in plants such as hops and cucumber, e.g. *Pseudoperonospora humuli* in hops; of the genus Bremia in plants such as lettuce, e.g. *Bremia lactucae* in lettuce; of the genus Pythium causing damping-off and root rots in a great number of plants, such as vegetables, sugar beets, ornamentals and conifers, e.g. *Pythium aphanidermatum* in sugar beets; of the genus Sclerospora in plants such as sorghum and corn, e.g. *Sclerospora sorghis* in sorghum.

For use in the method of the invention, the amount to be employed will vary depending on such factors as the species of fungi to be combatted, the time and nature of application and the amount and nature of the compound of formula I employed.

However, in general, satisfactory results are obtained when applied to a locus, e.g. on crops or to soil with a dosage rate in the range of from 0.05 to 5 kg, preferably from 0.1 to 3 kg particularly from 0.1 to 0.5 kg of a compound of formula I/ha treated locus, the application being repeated as required. When employed as a seed dressing, satisfactory results are obtained when applied at a rate of from about 0.05 to 0.5, preferably about 0.1 to 0.3 g compound of formula I/kg seed.

Depending on the circumstances, the compouns of formula I may be used in association with other pesticides e.g. fungicides, bactericides, insecticides, acaricides, herbicides or plant growth regulating agents in order to enhance their activity or to widen their spectrum of activity.

Fungicides particularly indicated for use in association with a compound of formula I are one or more compounds selected from a copper fungicide, fentin acetate, captan, folpet, mancozeb, maneb, zineb, propineb, cymoxanil, chlorothalonil, dichlofluanid and phosetyl-Al. Particularly useful associations comprise a compound of formula I, a compound selected from cymoxanil and phosetyl-Al and one or two compounds selected from copper-fungicide, captan, folpet, mancozeb, maneb, zineb, propineb, chlorothalonil, fentin acetate.

Examples of copper fungicides suitable for use in association with a compound of formula I are e.g. copper (II) carbonat, copper (II) sulphate and derivatives thereof such as copper (II) calcium sulphate, Bordeaux mixture and Burgundy mixture; copper (II) oxychloride and derivatives thereof such as copper (II) calcium oxychloride; tetracupric oxychloride, cuprous oxide, cupric hydroxide and also copper complexes such as copper triethanolamine hydroxide of the formula [Cu N(CH$_2$CH$_2$OH)$_3$]—(OH)$_2$, or bis(ethylenediamine)-copper (II) sulphate of the formula [Cu(H$_2$NCH$_2$CH$_2$NH$_2$)$_2$]SO$_4$, and mixtures thereof.

Fentin acetate, Chlorothalonil, Captan, Folpet, Mancozeb, Maneb, Zineb, Propineb, Dichlofluanid cymoxanil and phosetyl-Al are common names of known fungicides.

The compounds of formula I are conveniently employed as fungicidal compositions in association with agriculturally acceptable diluents. Such compositions also form part of the present invention. They may contain, aside from a compound of formula I as active agent, other active agents, such as fungicides. They may be employed in either solid or liquid forms e.g. in the form of a wettable powder, an emulsion concentrate, a water dispersible suspension concentrate ("flowable"), a dusting powder, a granulate, a delayed release form, incorporating conventional diluents. Such compositions may be produced in conventional manner, e.g. by mixing the active ingredient with a diluent and optionally other formulating ingredients such as surfactants.

The term diluents as used herein means any liquid or solid agriculturally acceptable material which may be added to the active constituent to bring it in an easier or improved applicable form, respectively to a usable or desirable strength of activity. It can for example be talc, kaolin, diatomaceous earth, xylene, or water.

Particularly formulations to be applied in spraying forms such as water dispersible concentrates or wettable powders may contain surfactants such as wetting and dispersing agents, e.g. the condensation product of formaldehyde with naphthalene sulphonate, an alkylarylsulphonate, a lignin sulphonate, a fatty alkyl sulphate, an ethoxylated alkylphenol and an ethoxylated fatty alcohol.

In general, the formulations include from 0.01 to 90% by weight of active agent from 0 to 20% by weight of agriculturally acceptable surfactant and 99.99 to 10% by weight (solid or liquid) diluent(s), the active agent consisting either of at least one compound of formula I or mixtures thereof with other active agents, such as fungicides. Concentrate forms of compositions generally contain between about 2 and 90%, preferably between about 5 and 70% by weight of active agent. Application forms of formulation may for example contain from 0.01 to 20% by weight, preferably from 0.01 to 5% by weight of active agent.

The invention is illustrated by the following examples wherein parts and percentages are by weight and temperatures are in °C.

Formulation Example I: Wettable powder

25 Parts of the compound of Example 1 hereinafter are ground with 3 parts of lauryl sulphate, 5 parts sodium lignin sulphonate, 22 parts of silica and 45 parts of finely divided kaolinite until the mean particle size is below 5 microns. The resulting wettable powder so obtained is diluted with water before use to a concentration of between 0.01% to 5% active agent.

The resulting spray liquor may be applied by foliar spray as well as by root drench application.

Formulation Example 2: Granules 0.5 Parts by weight of a binder (non-ionic tenside) is sprayed onto 94.5 parts by weight of quartz sand in a tumbler mixer and the whole thoroughly mixed. 5 Parts by weight of the compound of Example 1, hereinafter, are then added and thoroughly mixing continued to obtain a granulate formulation with a particle size in the range of from 0.3 to 0.7 mm. The granules may be applied by incorporation into the soil adjacent the plants to be treated.

Formulation Example 3: Emulsion Concentrate

25 Parts of a compound of formula I, e.g. the compound of Example 1, hereinafter, 65 parts of xylene, 10 parts of the reaction product of an alkylphenol with ethyleneoxide and calcium-dodecylbenzene sulphonate are thoroughly mixed until a homogeneous solution is obtained. The resulting emulsion concentrate is diluted with water before use.

FINAL PRODUCTS

Example 1:
N-(2-Butenoyl)-N-(2,4-dimethylthien-3-yl)-alanine-methylester

To 6.39 g (0.03 mol) of N-(2,4-dimethylthien-3-yl-alanine-methylester, 4.15 g (0.03 mol) of $K_2CO_3$, 10 ml of water and 100 ml of dichloromethane are added without cooling 3.14 g (0.03 mol) 2-butenoyl chloride.

After the exothermic reaction has subsided, stirring is continued for a further hour. Then the organic layer is separated, washed with water, dried over anhydrous $Na_2SO_4$ and evaporated in vacuo, to yield the title compound, $n_D^{20} = 1.5356$.

Example 2:
N-(Methoxyacetyl)-N-(2,4-dimethylthien-3-yl)alanine-methylester 5 g (0.025 mol) of N-(2,4-dimethylthien-3-yl)-methoxyacetamide in 45 ml of dry dimethylformamide (=DMF) are added dropwise to a well stirred suspension of 0.9 g (0.03 mol) of sodium hydride (80% dispersion in mineral oil) in 12 ml of dry DMF.

After the exothermic reaction (33°) has subsided the solution of the sodium salt is allowed to reach room temperature and then treated with 4.17 g (0.025 mol) of methyl-2-bromopropionate.

After the addition is completed the reaction mixture is heated at 50° for three hours and then evaporated to dryness. The residue is taken up with 100 ml to diethyl ether and filtered. The residual oil left on evaporating the filtrate is chromatographed on a silica gel column. Elution with diethylether-hexane 1:5 affords the title compound, having a m.p. of 42°–43°.

EXAMPLE 3

Following the procedure of either Example 1 or 2 but employing the appropriate compounds of formulae II and III (wherein Y' is Cl) or of formula IV and V (wherein L is Br) resp.

A. the following compounds of formula Im are obtained:

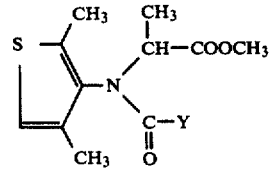

| Ex. | (Formula Im) Y | |
|---|---|---|
| 3.1 | $CH_2CH_2CH_3$ | ($n_D^{20}$ = 1.5128) |
| 3.2 |  | ($n_D^{20}$ = 1.5242) |
| 3.3 | 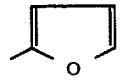 | ($n_D^{20}$ = 1.5570) |

-continued

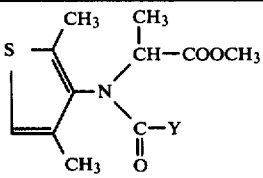

| Ex. | (Formula Im) Y | |
|---|---|---|
| 3.4 | 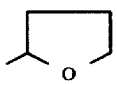 | |
| 3.5 | CH$_2$O—COCH$_3$ | (n$_D^{20}$ = 1.5090) |
| 3.6 | CH$_2$OCH$_2$CH=CH$_2$ | |
| 3.7 | CH$_2$OCH$_2$C≡CH | |
| 3.8 | CH$_2$—1,2,4-triazol-1-yl | |
| 3.9 | 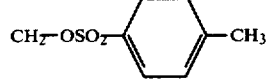 | (m.p. 91-93°) |
| 3.10 | CH$_2$OC$_2$H$_5$ | (b.p. 149-151°/0.02 Torr) |

B. The following compounds of formula In

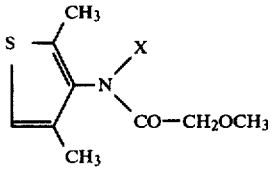

are obtained:

| Ex. | (Formula In) X | |
|---|---|---|
| 3.11 | CH(CH$_3$)CN | (n$_D^{20}$ = 1.5263) |
| 3.12 | CH(CH$_3$)—C≡CH | (n$_D^{20}$ = 1.5374) |
| 3.13 | CH(CH$_3$)—CH=CH$_2$ | (n$_D^{20}$ = 1.5297) |
| 3.14 | CH$_2$COOCH$_3$ | (n$_D^{20}$ = 1.5228) |
| 3.15 |  | |
| 3.16 | CH(CH$_3$)—CONHOCH$_3$ | |
| 3.17 | CH$_2$—C$_6$H$_5$ | (n$_D^{20}$ = 1.5647) |
| 3.18 | 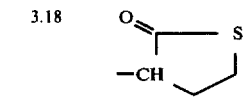 | |

C. The following compounds of formula Io

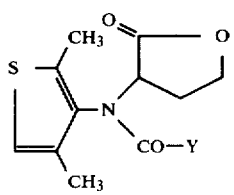

are obtained:

| Ex. (Formula Io) | Y | Ex. | (Formula Io) Y |
|---|---|---|---|
| 3.19 | CH$_2$OCH$_3$ m.p. 131-134° | 3.23 | 2-furyl |
| 3.20 | CH$_2$OC$_2$H$_5$ | 3.24 | CH$_2$—SCH$_3$ |
| 3.21 | CH$_2$CH$_2$CH$_2$CH$_3$ (n$_D^{20}$ = 1.5338) | 3.25 | CH$_2$—C$_6$H$_5$ |
| 3.22 | cyclopropyl (very sticky honey) | 3.26 | CH$_2$Cl (m.p. 117-119°) |

D. The following compounds of formula Ip

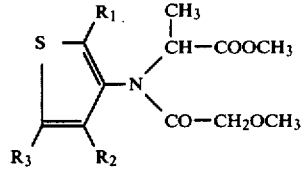

| Ex. (Formula Ip) | R$_1$ | R$_2$ | R$_3$ | m.p./b.p./ n$_D^{20}$ |
|---|---|---|---|---|
| 3.27 | CH$_3$ | OCH$_3$ | H | 75-76° |
| 3.28 | CH$_3$ | OCH$_3$ | Br | 56-58° |
| 3.29 | SCH$_3$ | CH$_3$ | H | 142°/0.001 Torr |
| 3.30 | H | CH$_3$ | H | |
| 3.31 | Br | CH$_3$ | Br | |
| 3.32 | CH$_3$ | CH$_3$ | Br | |
| 3.33 | SCH$_3$ | CH$_3$ | Br | 85° |
| 3.34 | C$_2$H$_5$ | C$_2$H$_5$ | H | n$_D^{20}$ = 1.5204 |
| 3.35 | C$_2$H$_5$ | CH$_3$ | CH$_3$ | n$_D^{20}$ = 1.5179 |
| 3.36 | CH$_3$ | CH$_3$ | CH$_3$ | n$_D^{20}$ = 1.5193 |
| 3.37 | CH$_3$ | OCH$_3$ | Cl | |
| 3.38 | CH$_3$ | CH$_3$ | Cl | |
| 3.39 | CH$_3$ | CH$_3$ | COOCH$_3$ | 82-83° |
| 3.40 | COOCH$_3$ | CH$_3$ | H | 53-55° |

E. The compound of formula I wherein X is tetrahydro-2-furanone-3-yl and Y is CH$_2$OCH$_3$:

| 3.41 | R$_1$ = 2-SCH$_3$, R$_2$ = 4-CH$_3$ and R$_3$ = H | (m.p. 120°) |
| 3.42 | R$_1$ = 2-SCH$_3$, R$_2$ = 4-CH$_3$ and R$_3$ = 5-Br | (m.p. 99°) |
| 3.43 | R$_1$ = 2-SCH$_3$, R$_2$ = 4-CH$_3$ and R$_3$ = 5-Cl | (m.p. 102-103°) |

F. The following compounds of formula I wherein X is CH(CH$_3$)COOCH$_3$ and Y is n-propyl:

| 3.44 | R$_1$ = 2-CH$_3$, R$_2$ = 4-OCH$_3$ and R$_3$ = H |
| 3.45 | R$_1$ = 2-CH$_3$, R$_2$ = 4-OCH$_3$ and R$_3$ = 5-Cl |
| 3.46 | R$_1$ = 2-CH$_3$, R$_2$ = 4-OCH$_3$ and R$_3$ = 5-Br. |

EXAMPLE 4: Methyl 2-(2,4-dimethylthien-3-yl)-2-(methoxyacetyl)-1-methyl-hydrazinecarboxylate (process c)

0.73 g (0.03 mol) NaH and 7.95 (0.03 mol) methyl 2-(2,4-dimethylthien-3-yl)-2-(methoxyacetyl)-hydrazinecarboxylate in 100 ml dry toluene are heated under reflux for 3 hours. The reaction mixture is then, together with 9.52 g (0.067 mol) CH$_3$J, transferred into a sealed cylinder and heated 20 hours at 110°. The mixture is, after cooling, diluted with diethylether, washed with water, dried and evaporated to yield the title compound.

EXAMPLE 5:
2-Methoxy-N-(2,4-dimethylthien-3-yl)-N-2-oxo-3-oxazodidinyl)-acetamide (process d)

Step α

A solution of 24.85 g (0.1 mol) of 2-chloroethyl 2-(2,4-dimethylthien-3-yl)-hydrazinecarboxylate in 150 ml dry toluene is treated with 10.85 g (0.1 mol) methoxyacetylchloride, and the mixture is heated to 80° for 2 hours, vigorous HCl-formation starting at approx. 50° C. The mixture is cooled to room temperature, washed subsequently with water, 10% aqueous NaHCO$_3$-solution and water, dried over MgSO$_4$ and evaporated in vacuo to yield the compound 2-chloroethyl 2-(methoxyacetyl)-2-(2,4-dimethylthien-3-yl)hydrazinecarboxylate, which may be directly reacted with NaOCH$_3$ (see Step β).

Step β

A solution of 32.05 g (0.2 mol) of 2-chloroethyl 2-(methoxyacetyl)-2-(2,4-dimethylthien-3-yl)-hydrazinecarboxylate in 150 ml methanol is slowly added to a solution of 5.4 g (0.1 mol) sodium methanolate in 50 ml methanol at room temperature. The mixture is stirred for 1 hour at room temperature, and then concentrated in vacuo. The residue is dissolved in dichloromethane, washed with water, dried over Na$_2$SO$_4$, and the solvent evaporated in vacuo to yield the title compound.

EXAMPLE 6

As described in Example 5, but using the appropriate starting materials, the following compounds of the formula Iq are prepared.

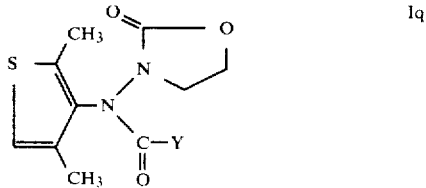

| Ex. | (Formula Iq) Y |
|---|---|
| 6.1 | cyclopropyl |
| 6.2 | CH=CH—CH$_3$ |
| 6.3 |  |
| 6.4 | CH$_2$Cl |

EXAMPLE 7:
2-Methoxy-N-(2,4-dimethylthien-3-yl)-N-(1,2-pentadien-4-yl)-acetamide (process e)

To a solution of 10.0 g (0.04 mol) 2-methoxy-N-(2,4-dimethylthien-3-yl)-N-(1-butin-3-yl)acetamide in 80 ml dioxan are added 1.92 g (0.064 mol) paraformaldehyde, 4.85 g (0.048 mol) diisopropylamine and 1.89 g cuprous bromide and the mixture heated to reflux for 6 hours. The mixture is cooled to room temperature, filtered, evaporated in vacuo, the residue partitioned between ethylacetate and 1 M aqueous citric acid solution, the organic phase separated, washed subsequently with a saturated aqueous NaHCO$_3$-solution, water, is dried over MgSO$_4$ and the solvent evaporated in vacuo.

EXAMPLE 8:
N-(hydroxyacetyl)-N-(2,4-dimethylthien-3-yl)-alanine-methylester (process f)

A solution of 5.4 g (0.1 mol) sodium methanolate in 50 ml dry methanol is slowly added to a mixture of 62.6 g (0.2 mol) N-(acetoxyacetyl)-N-(2,4-dimethylthien-3-yl)-alanine methylester (=Ex. 3.5) in 750 ml dry methanol with stirring. The mixture is stirred for two hours at room temperature, then freed of solvent in vacuo. The residue is poured into water and the pH adjusted to pH 2 with 2 N aqueous HCl. The product is extracted with CHCl$_3$, the organic phase washed with water, dried over Na$_2$SO$_4$, and evaporated in vacuo to yield the title compound, m.p. 69°-70°.

EXAMPLE 9:
N-(2,2-dimethylhydrazino-acetyl)-N-(2,4-dimethylthien-3-yl)-alanine-methylester (process g)

A mixture of 8.5 g (0.02 mol) N-[(4-methylphenyl)-sulphonyloxyacetyl]-N-(2,4-dimethylthien-3-yl)-alanine-methylester (=Ex. 3.9) and 2.4 g (0.04 mol) 1,1-dimethylhydrazine in 150 ml ethanol is refluxed for four hours, then evaporated in vacuo, the residue taken up in dichloromethane, washed subsequently with water, aqueous 1 N HCl and water, dried over MgSO$_4$, and evaporated in vacuo to yield the title compound.

EXAMPLE 10:
N-(2,3-Oxidobutanoyl)-N-(2,4-dimethylthien-3-yl)-alanine-methylester (process h)

3.9 g (13.9 mol) N-(2-butenoyl)-N-(2,4-dimethylthien-3-yl)-alanine-methylester in 40 ml methanol and 3.5 g hydrogen peroxide (40% solution in water) are cooled to 15° with stirring, while a solution of 0.28 g (7 mmol) sodium hydroxide in 12 ml water is slowly added. The mixture is stirred for one hour at 20°, then poured into 500 ml water, extracted with dichloromethane, the organic phase washed with water, dried over Na$_2$SO$_4$, and the solvent evaporated in vacuo to yield the title product compound, (n$_D^{20}$=1.5243).

EXAMPLE 11:
2-Methoxy-N-(2,4-dimethylthien-3-yl)-N-(1-iodo-1-butin-3-yl)-acetamide (process i)

A mixture of 2.51 g (0.01 mol) 2-methoxy-N-(2,4-dimethylthien-3-yl)-N-(1-butin-3-yl)-acetamide, 1.3 g (0.0325 mol) NaOH and 100 ml methanol are cooled with stirring to 10°, and 2.65 g (0.01 mol) powdered iodine is then slowly added. The mixture is then stirred for 3 hours at room temperature, neutralized with methanolic HCl-solution, and the solvent evaporated to yield, after chromatography, the title compound.

EXAMPLE 12:
N-(Dimethylaminosulphonyloxyacetyl)-N-(2,4-dimethylthien-3-yl)-alanine-methylester 8.13 g (0.03 mol) N-(hydroxyacetyl)-N-(2,4-dimethylthien-3-yl)-alanine-methylester is added in portions to a slurry of 1.05 g (0.035 mol) sodium hydride (80% in mineral oil) in 50 ml dry dimethoxyethane with stirring at 10°-15° under a blanket of nitrogen. The mixture is stirred at room temperature for half an hour, and then are added 4.3 g (0.03 mol) dimethylsulphamic acid chloride. The mixture is stirred for 18 hours at 50°, then cooled to room temperature, filtered, concentrated in vacuo, the residue taken up in CHCl₃, washed thoroughly with water, dried over MgSO₄ and evaporated in vacuo to yield the title compound.

INTERMEDIATES

EXAMPLE 13:

N-(2,4-Dimethylthien-3-yl)-methoxyacetamid

To 12.7 g (0.1 mol) of 2,4-dimethyl-3-aminothiophene, 13.84 g (0.1 mol) of K₂CO₃, 50 ml of water and 160 ml of methylene chloride are added without cooling 10.8 g (0.1 mol) of methoxyacetyl chloride.

After the exothermic reaction has subsided stirring is continued for a further hour. Then the organic layer is separated, washed with water, dried over anhydrous Na₂SO₄ and evaporated in vacuo. The crystalline residue is triturated with diethyl ether, yielding the analytically pure title compound, m.p. 62°–63°.

EXAMPLE 14:

N-(2,4-dimethylthien-3-yl)-alanine-methylester

A mixture of 12.7 g (0.1 mol) 2,4-dimethyl-3-aminothiophene, 13.84 g (0.1 mol) K₂CO₃ and 16.7 g (0.1 mol) methyl 2-bromopropionate in 200 ml dimethylformamide are stirred over night at 80°. The mixture is cooled, filtered, evaporated, the residue dissolved in dichloromethane, washed with water, dried and evaporated to yield the title compound, m.p. 33°–34°.

EXAMPLE 15: 2,4-Dimethyl-3-aminothiophene

To 890 ml (3 mols) of sodium bis(2-methoxyethoxy)aluminium hydride (70% solution in toluene) and 600 ml of dry toluene is added dropwise with vigorous stirring a solution of 100 g (0.58 mols) of methyl 3-amino-4-methylthiophene-2-carboxylate (DAS 1,083,830) in 700 ml of dry toluene at such a rate that the temperature does not rise above 55°.

After the addition is complete stirring is continued for a further 30 minutes and the reaction mixture then cautiously added in small portions at 0° to 1200 ml of 20% potassium hydroxide solution.

The toluene layer is separated, dried (MgSO₄) and evaporated in vacuo. The residual brown liquid is distilled under diminished pressure, affording the analytically pure title compound, b.p. 49°–52°/0.01 Torr.

EXAMPLE 16: Methyl 2-(2,4-dimethylthien-3-yl)-hydrazinecarboxylate

To a mixture of 35.5 g (0.25 mol) 2,4-dimethylthien-3-yl-hydrazine, 27.6 g (0.35 mol) pyridine and 83 ml water are added within 15 minutes at room temperature 23.6 g (0.25 mol) methyl chloroformiate. 83 ml water are further added, and the mixture is stirred for 3 hours at room temperature. After the addition of 300 ml diethylether, the mixture is acidified with 2 N HCl, the organic phase separated, washed with water, dried and concentrated.

EXAMPLE 17

Analogous to Example 16, but using 2-chloroethyl chloroformate instead of methyl chloroformate, 2-chloroethyl 2-(2,4-dimethylthien-3-yl)-hydrazinecarboxylate is obtained.

What we claim is:

1. A compound of formula I

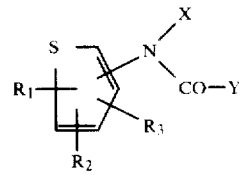

wherein $R_1$, $R_2$ and $R_3$, independently, are H, $C_{1-4}$alkyl, $C_{1-4}$alkoxy, $C_{1-4}$alkylthio or halogen selected from F, Cl and Br, X is selected from a group —CH(R₄)—R₅ or a group —N(R₆)—COOR₇, in which $R_4$ is H or $C_{1-4}$alkyl, $R_5$ is COZR₈, CO—N(R₉)OR₁₀, CN, CHO,

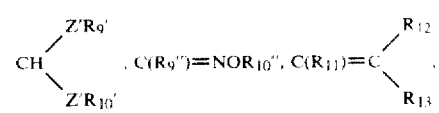

C≡C—R₁₄, allenyl; or is 2,2-dihalo-1-cyclopropyl unsubstituted or substituted by $C_{1-4}$alkyl; or is phenyl unsubstituted or substituted.

$R_6$ is $C_{1-3}$alkyl, $R_7$ is $C_{1-6}$alkyl, $C_{3-6}$alkenyl or $C_{3-6}$alkinyl, whereby $R_6$ and $R_7$ may be linked together to form CH₂—CH₂;

and wherein

Z and Z' are O or S $R_8$ is $C_{1-6}$alkyl, $C_{3-6}$alkenyl, or $C_{3-6}$alkinyl, and whereby ZR₈ may be linked with R₄ to form the bridge ZCH(R₁₅)—CH₂ in which Z is as defined above and R₁₅ is H or CH₃;

$R_9$, $R'_9$ and $R''_9$ are H or $C_{1-4}$alkyl, $R_{10}$, $R'_{10}$ and $R''_{10}$ are $C_{1-4}$alkyl, whereby R₉ may be linked with R₁₀, resp. R'₉ with R'₁₀, resp. R''₉ with R''₁₀ and signify alkylene, to form a 5- or 6-membered heterocyclic ring, $R_{11}$, $R_{12}$, $R_{13}$, independently, are H, $C_{1-4}$alkyl, or halogen selected from F, Cl or Br, $R_{14}$ is H, $C_{1-4}$alkyl or halogen selected from Cl, Br or I, and Y is H; a hydrocarbon selected from $C_{1-6}$alkyl, $C_{2-6}$alkenyl and $C_{2-6}$alkinyl unsubstituted or substituted by halogen, selected from F, Cl or Br, or by CN;

$C_{2-6}$epoxyalkylene; $C_{3-6}$cycloalkyl; a 5-membered heterocyclic ring comprising 1 to 3 heteroatoms selected from O, S and N, which in unsubstituted or substituted by $C_{1-4}$alkyl or halogen selected from F, Cl or Br;

(A)ₙ—Az; (A)ₙ—Y₁—NR₉ₐR₁₀ₐ;

(A)ₙZ₁H and esters or ethers thereof;

benzyl unsubstituted or substituted, in which

A is CH₂ or CH(CH₃)

n is 0 or 1,

Az is a 1-azolyl comprising 1 to 3 nitrogen atoms,

Y₁ is a covalent bond or NH, $R_{9a}$ is H or $C_{1-4}$alkyl, $R_{10a}$ is $C_{1-4}$alkyl, Z₁ is O or S.

2. A compound of claim 1, wherein
—N(X)COY is in the 3-position of the thiophene ring, $R_1$ and $R_2$ are in 2,4-position of the thiophene ring and are selected from $CH_3$, Cl, $OCH_3$ and $SCH_3$ and $R_3$ is H, Cl or Br.

3. A compound of claim 2, wherein X is $CH(CH_3)COOCH_3$ or tetrahydro-2-furanone-3-yl.

4. A compound of claim 2, wherein X is 2-oxo-3-oxazolidinyl or $N(CH_3)COOCH_3$.

5. A compound of claim 3 wherein Y is $CH_2OH$, $CH_2OCH_3$, $CH_2OC_2H_5$, $CH_2OCH_2CH=CH_2$, $CH_2OCH_2C=CH$, $CH_2OCH_2OCH_3$, $CH_2OSO_2N(CH_3)_2$, $CH_2Cl$, $n-C_3H_7$, $n-C_4H_9$, cyclopropyl, $CH=CH-CH_3$, 2-furyl, benzyl or 2-tetrahydrofuryl.

6. A compound of claim 5, wherein X is $CH(CH_3)COOCH_3$, $R_1$ is 2-$SCH_3$, $R_2$ is 4-$CH_3$ and $R_3$ is H.

7. A compound of claim 5, wherein X is $CH(CH_3)COOCH_3$, $R_1$ is 2-$CH_3$, $R_2$ is 4-$OCH_3$ and $R_3$ is 5-Br.

8. A compound of claim 5, wherein X is $CH(CH_3)COOCH_3$, $R_1$ is 2-$SCH_3$, $R_2$ is 4-$CH_3$ and $R_3$ is 5-Br.

9. A method of combatting phytopathogenic fungi which comprises applying to the locus thereof a fungicidally effective amount of a compound of claim 1.

10. A fungicidal composition comprising a compound of formula I as defined in claim 1 in association with an agriculturally acceptable diluent.

* * * * *